United States Patent [19]

Jones

[11] 4,214,155
[45] Jul. 22, 1980

[54] SYSTEM FOR DETECTING POSITION OF GAUGE POINTER

[75] Inventor: George D. Jones, Deerfield, Wis.

[73] Assignee: Airco, Inc., Montvale, N.J.

[21] Appl. No.: 899,929

[22] Filed: Apr. 26, 1978

[51] Int. Cl.² .............................................. G01D 5/34
[52] U.S. Cl. .................. 250/231 R; 250/227
[58] Field of Search ..................... 250/231 R, 227, 239

[56] References Cited

U.S. PATENT DOCUMENTS

| | | | |
|---|---|---|---|
| 2,521,479 | 9/1950 | Rautter | 250/231 R |
| 2,659,563 | 11/1953 | Saxe | 250/231 R |
| 3,329,825 | 7/1967 | Enright | 250/231 R |
| 3,332,014 | 7/1967 | Orths et al. | 250/231 R |
| 3,596,178 | 7/1971 | Skylaruk et al. | 250/231 R |

Primary Examiner—David C. Nelms
Attorney, Agent, or Firm—Roger M. Rathbun; Edmund W. Bopp; Larry R. Cassett

[57] ABSTRACT

A system is disclosed for detecting the position of the pointer of a gauge. The system includes a stationary light source which is positioned adjacent the pointer. A lens receives the light from the light source and redirects the light in at least one elongated light beam directed toward the pointer. In the preferred embodiment, the light source is located along the pointer's axis of rotation and the lens bends the light rays 90° to form at least one arcuate light beam. A plurality of elongated light beams can be used and variations of different shapes of light beams can readily be used by so designing the lens means. A light sensitive detector is positionable in the gauge itself and is movable along a guided path on the opposite side of the pointer than is the light source. The guided path generally follows the particular shape of light beams that is directed toward the needle. The function of the light detector is to sense, and provide some signal when the pointer passes across the sensor, thereby substantially reducing the amount of light directed toward the sensor. In this manner the detector signals the position of the pointer. The sensor may be moved within limits to an infinite number of positions along the elongated light beam by conveniently located knobs outside the gauge. The operator thus can, by simply turning a knob, adjust a sensor to a desired position and the sensor will detect when the gauge pointer passes or remains at that position.

8 Claims, 6 Drawing Figures

SYSTEM FOR DETECTING POSITION OF GAUGE POINTER

BACKGROUND OF THE INVENTION

The invention relates generally to meters having indicating pointers, and more particularly, to a system for detecting the location of the pointer.

There has been divised many types of meters having means to detect the position or movement of the pointer, however, most suffer from one or more detriments as a result of the detecting means. Basically they can be broken down into broad categories as contacting and non-contacting type. In the contacting type of detecting means, the needle makes physical contact with the detecting means and such contact may make or break an electrical switch so that the needle contact is sensed.

The contact type of detecting systems generally have the inherent problem that the physical contact in some way affects the otherwise free movement of the pointer. In most sensitive meters, a great deal of stress is put on the lack of friction in the movement to minimize any forces which could impede free movement of the pointer to insure that, to the extent possible, the pointer movement precisely responds to the particular parameter that the pointer is sensing.

In the non-contact type of detecting system, some means is employed such that there is no physical contact between that means and the pointer. Most popular of the non-contacting type detecting systems include magnetic pick-ups and photoelectric devices. It is the latter method to which the present invention pertains.

Prior art detecting systems of the photoelectric type have included various means. For example, one such system includes an individual light source and individual light detector. The light source is aimed at a particular position and, as the pointer passes that position, the light is reflected off the pointer to the light detector. A difficulty, of course, of such detecting system is the lack of easy adjustment in the event some other pointer position is desired. Both the light source and light detector must then be carefully adjusted such that the new position be sensed. Alternatively, for different positions, one could utilize a plurality of such individual light sources, accurately directed toward a plurality of light sensors.

Obviously, the difficulties of plurality of sensors and detectors increases as does the number of such sensor and detectors as each must be accurately set to the desired pointer location and one still must sacrifice the possibility of sensing a pointer position intermediate an individual light source and light detector. Since the number of such sources, etc. must be finite, the number of detectable positions also is finite.

As a further example of the prior art, other arrangements have placed the light source on the end of the pointer itself such that the light source moved with the pointer and thus could be detected in various positions of the pointer, with the light detector being adjustable to such various positions. A difficulty in such arrangement involves the difficult task of replacing such bulb and in the cost of manufacturing and installing a pointer with a light source at its end. Also, since many gauges having pointers are extremely sensitive, it is disadvantageous to add any weight to the pointer in that it thus adds additional drag to the pointer bearings and can slow the needle movement in responding to a change in the sensed parameter.

Other difficulties inherent in prior art methods when light sources and/or light detectors are used outside the face of the gauge include a lessening of the visibility of the gauge pointer. In instances where the gauge is monitored by a person such that undistorted visibility is a must, the face must be as uncluttered as possible by any interfering devices.

SUMMARY OF THE INVENTION

Now, in accordance with the present invention, the foregoing difficulties inherent in the prior art pointer detecting systems are overcome and there is thus achieved an economical system having a maximum degree of adjustability yet such adjustment can be made with ease by an operator. A single, stationary light source is provided on the outside of the gauge and which directs light into a lens located between the light source and its pointer of a gauge. The purpose of the lens is to modify the light from the light source such that an elongated beam of light is formed and which is directed toward the pointer. Behind the pointer, that is, located opposite the light source with respect to the pointer is a light sensor. The sensor is infinitely adjustable along a path generally coextensive with the elongated light beam.

The elongated light beam therefore provides a source of light directed at the pointer along a path and, since the sensor is movable along that path, the sensor can be placed in an infinite number of positions along that path. As the pointer moves in response to a sensed parameter, it also travels along the path of the elongated light beam of light directed toward the light sensor along that path at any point thereon where the sensor has been prepositioned by an operator.

The advantages of the present system with respect to the prior art are thus apparent.

The light source itself may be of a conventional light, readily obtainable and, since its location is outside of the particular gauge, it may easily be changed by the operator in case it burns out. A bulb failure is instantly recognizable. The position of the light source is fixed and need not be altered or moved in any way thereafter by the user to redirect its light either in initial setup or for any desired changes in operation or set point.

The lens is also easily manufactured of plastic and is adaptable to different needle movements. For instance, the present invention is shown as a dial guage when the pointer rotates about an axis. The lens system therefore produces arcuate light beams directed toward the pointer, however, the lens can easily be manufactured to produce a straight elongated beam to accommodate other types of meters. Also, the lens may produce a plurality of elongated light paths of varying lengths and positions in order to allow the use of a plurality of sensors located, for example, on different radii about a radially moving type gauge pointer.

The lens may be transparent in its entirety, thus creating no obstruction to the dial visibility. The light sensor can be of generally conventional design since the needed sensitivity can be achieved by devices currently on the market. Since the lens creates a concentrated elongated light beam, the difference in light intensity can be readily sensed when the beam is interrupted by the pointer, yet the light sensors can operate under normal outside light without causing a false detection or impairing a legitimate detection if one should occur. Therefore, the effect of outside light is essentially minimized.

Since the light to be sensed is in the form of an elongated beam, a single light sensor may be used in each such beam and yet the position of that sensor may be varied in an infinite number of positions along the beam. The movement and setting of the light sensor position is accomplished through a knob located on the face of the gauge, therefore its setting can be easily made by the operator without taking the gauge apart. Also, when set, the actual setting can be visually perceived by the user and its location determined in accordance with the indicia on the dial itself. Thus, for example, if the operator desires to detect the movement of the pointer past a particular setting, i.e. 80 psi, he actually moves and sets the light sensor to 80 psi.

The system disclosed herein has further overall advantages, in that the system is independent of the gauge mechanism, thus it does not impose any drag on the pointer operation. It can therefore be used with the most sensitive instruments without affecting the accuracy or response. In addition, the system not only allows an individual light sensor to be infinitely adjustable about a 360° radial dial, but can employ a plurality of such sensors to be placed around the 360° arc, either in the same radius of travel or in a plurality of radii in case some overlapping settings are devised.

Finally, the detecting setting of the present invention can be retrofitted to conventional gauges rather than require manufacturing of a complete gauge and detecting system. The system is thus adaptable to different kinds of gauges without requiring an entire manufacturing change to build various gauges such as ammeters, voltmeters, pressure gauges and the like.

The foregoing and other advantages and features of the present invention will become readily apparent from the following description.

BRIEF DESCRIPTION OF THE DRAWINGS

The invention is diagramatically illustrated by way of example in the drawings appended hereto; in which.

DESCRIPTION OF THE PREFERRED EMBODIMENT

Figure 1:
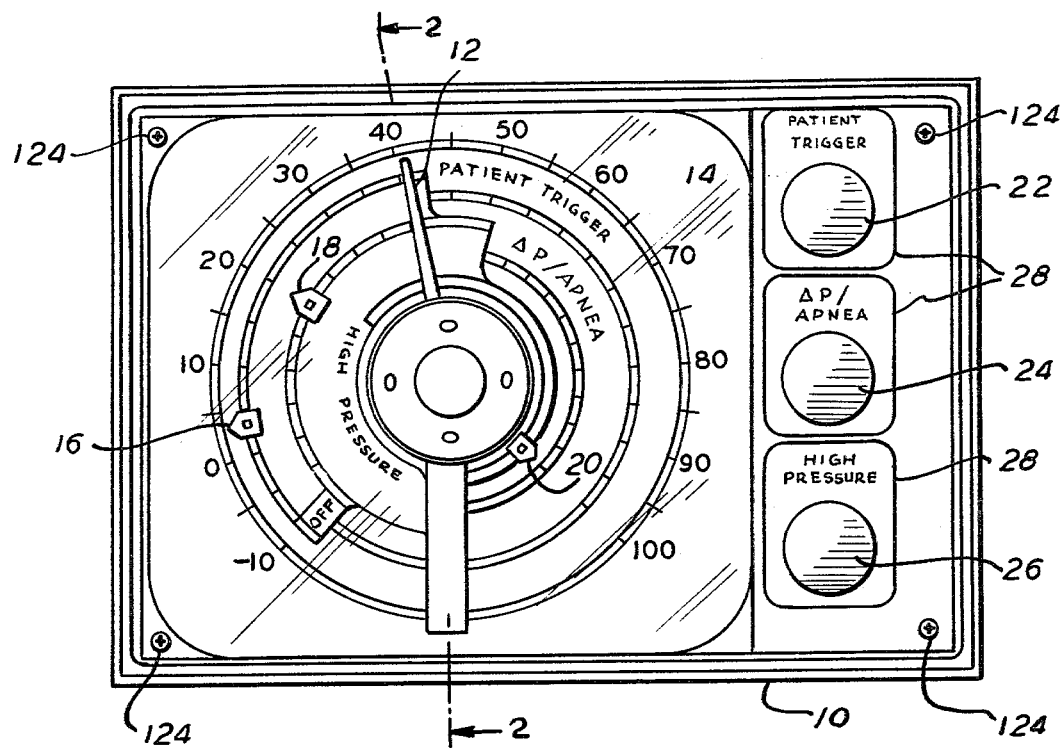
FIG. 1 is a front view of a gauge incorporating the pointer detecting system in accordance with the present invention.

In FIG. 1 there is shown a gauge 10 having incorporated thereon, a system for detecting the position of its pointer 12. The faceplate 14 of the gauge 10 has printed thereon certain indicia depending upon the particular type of gauge or meter concerned. The present invention will be described in terms of a pressure gauge used on a medical respirator and having a radially moving pointer, however, the detecting system can obviously be used on most types of gauges, or meters, or dials, including ammeters, voltmeters, pressure gauges, vacuum gauges and the like. It is to be noted, however, that the use of this detecting system on a medical respirator is believed particularly beneficial to a respirator by offering certain centralized control settings that constitute an improvement in a respirator. As noted on the particular indicia of FIG. 1, the numbers refer to pressure in $CMH_2O$ and the gauge 10 itself is a compound gauge, that is it measures both positive and negative pressures (vacuum).

As shown, therefore, such indicia range from a $-10$ $CMH_2O$ to an upper point of 100 $CMH_2O$. A plurality of set point indicators are positioned about the faceplate 14, and represent various set points of the patient trigger indicator 16, $\Delta p$ indicator 18, and high pressure indicator 20, the function of the indicators to be later explained. Each of the indicators 16, 18 and 20 correspond, however, to setting knobs 22, 24 and 26 which extend forward from the gauge 10. Each knob 22, 24 and 26 includes suitable labeling 28 to indicate its particular function to the user.

Figure 2:
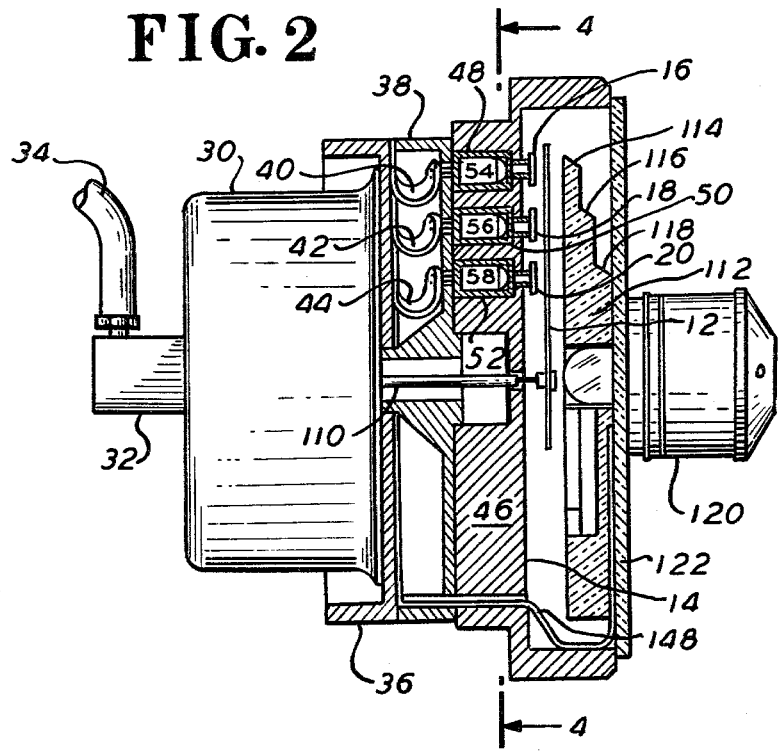
FIG. 2 is a cross-sectional view taken along the line 2—2 of FIG. 1.

Turning now to FIG. 2, in cross-section, the various components of the detection system are shown on a standard pressure gauge having housing 30 containing the normal elements of a diaphragm type pressure gauge. The internal workings of the pressure gauge within housing 30 are not shown inasmuch as such workings can be readily purchased and form no part of the present invention except for the normal operation of a pressure gauge. The housing 30 has some suitable inlet connection 32 which is connectible to tubing 34 through which the pressure signals are transmitted to gauge 10.

A gauge mount 36 is attached to the housing 30 to provide support for remaining structure of the detection system. The gauge mount 36 normally has drilled holes (not shown) to receive cap screws (not shown) which screws the gauge mount 36 in place to threaded holes within housing 30, which threaded holes are normally used in conventional pressure gauges to receive similar cap screws which serves to secure the front dial containing portion thereto.

There is mounted upon gauge mount 36, a circuit housing 38 which serves to provide room for movement of flex circuits 40, 42 and 44, the function of which will be later explained.

A main housing 46 is affixed to circuit housing 38 by suitable means (not shown) and has a plurality of arcuate shaped grooves 48, 50 and 52 formed therein. As previously explained, the detecting system may be utilized with a singular groove and, in addition, may be straight rather than arcuate, however, in the device being described and which was designed for a medical respirator, a plurality of grooves has been used.

Each of grooves 48, 50 and 52 form the arcs of a circle having the same center point but having different radii. The grooves 48, 50 and 52 each have a narrower width portion toward the front surface of housing 46 on which the faceplate 14 is secured.

Within each of the grooves 48, 50 and 52 there is positioned a light detector means 54, 56 and 58 respectively which are adapted to slide within said grooves.

Figure 3:
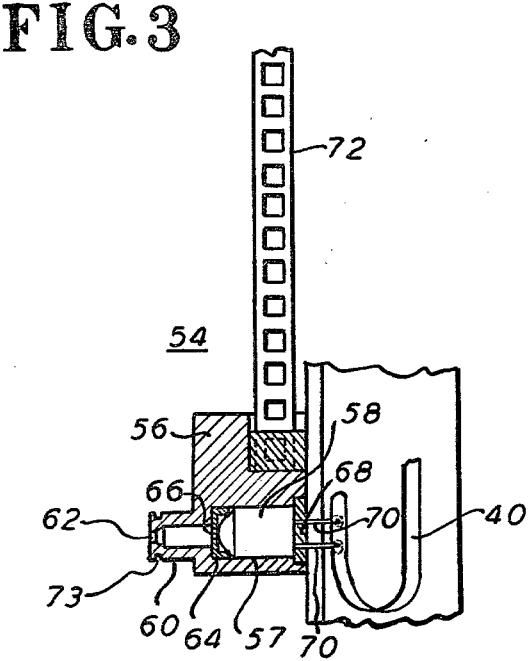
FIG. 3 is a cross-sectional view taken along the lines 3—3 of FIG. 2.

In FIG. 3, one of the light detector means 54 is shown in detail, which is typical of each of the light detector means used herein. The light detector means 54 includes a molded carriage 56 having a recess 57 within which is placed a light sensor 58. The light sensor 58 is of commercially available miniature type, solid state and which transmits a signal upon light impinging upon its light sensitive surface.

The light detector means 54 further includes a forward extension 60 which is adapted to fit within the narrower width portion of groove 48 in FIG. 2. The main body of light detector means 54 fits within the wider portion of grooves 48 such that the light detector means 54 slides freely within groove 48 yet is also contained therein. A tiny front opening 62 is formed in the forward extension 60 to receive light as will be explained. A mask 64, also having a tiny aligned opening 66 is fitted within the recess 56 and held thereon by the light sensor 58. As will later become apparent, the two aligned openings 62 and 66 serve to prevent the undesired entrance of light from any other extraneous source other than the intended light source.

The light sensor 58 is retained within recess 56 by means such as staking with hot soldering iron at 68. Suitable electrical leads 70 extend to connect to the flex-circuit 40.

The other end of flex-circuit 40, as well as flex-circuits 42 and 44 in similar manner, extend to a mounted circuit board (not shown) and thence are fed, externally to the gauge 10, to suitable electronic circuitry. The electronic circuitry is not shown since normal, state of art, amplifiers can be used to detect the signal from one of the light sensors to thereafter provide a useful signal.

A carriage drive strap 72 is affixed to light detector means 54 and extends therefrom, the purpose of which will be later explained.

To complete the description of the light detector means, a small groove 73 is formed in the outer end of forward extension 60 and which is adapted to receive an indicator 16 after the light sensor is installed within the groove 48.

Figure 4:
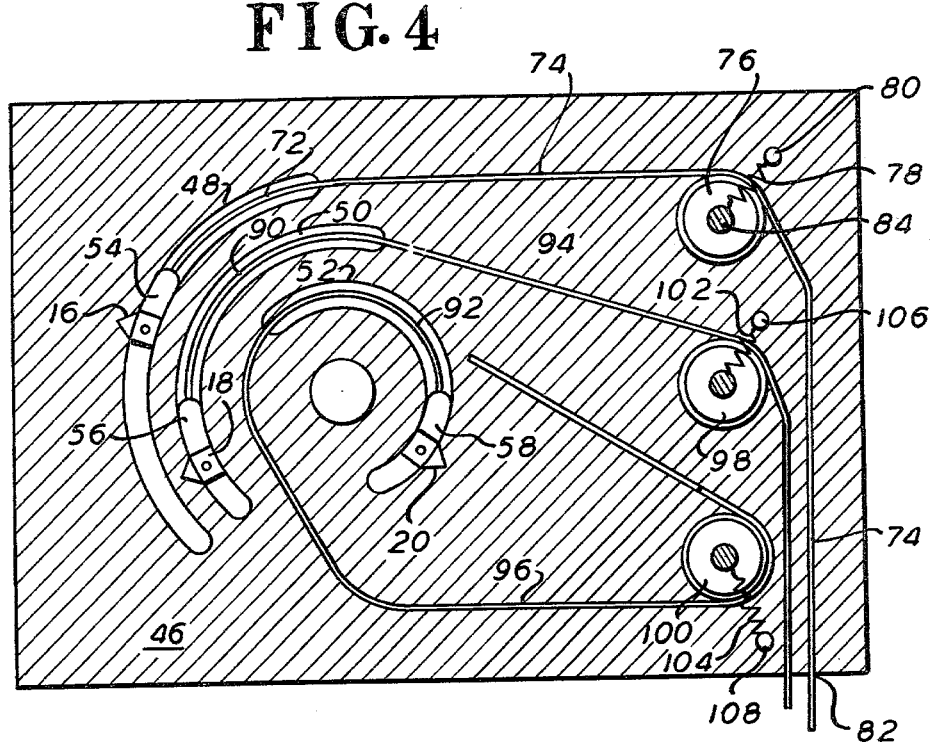
FIG. 4 is a schematic view showing the path of light directed by the lens used on the present invention.

Turning briefly to FIG. 4, the mechanism for moving the light detector means 54 may be described. As shown, the carriage drive strap 72 extends from light detector means 54 through the groove 48 and enters a curved channel 74 formed in housing 46. The carriage drive strap 72 is engaged by a roller 76 which is retained in frictional engagement by means of spring 78 attached between the roller 76 and a post 80 to bias the roller 76 toward the carriage drive strap 72 to maintain good frictional engagement therebetween. The carriage drive strap 72 thereafter continues in channel 74 and, depending upon the desired radial movement of light detector means 54, may even be permitted to extend external of housing 46 through opening 82.

The roller 76 rotates about its shaft 84 on which is secured the knob 22, shown in FIG. 1. Accordingly, as the knob 22 is turned by a user, roller 76 also rotates and serves to move carriage drive strap 72 in channel 74, thereby causing corresponding movement of light detector means 54.

As previously shown on FIG. 1, the indicator 16 which is affixed to light detector means 54 thereby can be moved to any desired position along the groove 48 and the indicator 16 will show on the face plate 14 indicia, that setting (in this case, pressure) at which the light detector means 54 is positioned.

In similar manner, the remaining light detector means 56 and 58, also having indicators 18 and 20 respectively, can each be moved within their respective grooves 50 and 52 by carriage drive straps 90 and 92 moving through their channels 94, 96. In each instance a suitable roller, shown as 98 and 100, drive the carriage straps 90 and 92 by frictional engagement and by springs 102 and 104 secured to posts 106 and 108. As may be seen with respect to the carriage drive strap 92, due to the relatively short desired distance in which light detector means 58 moves, the carriage drive strap 92 may end within the confines of the housing 46.

Hence, the knobs 22, 24 and 26 may be rotated to a desired position by an operator, and in doing so, the light detecting means 54, 86 and 88 will be correspondingly moved to the proper position. The operator can visually ascertain the exact position of each individual light detecting means by noting the position of pointers 16, 18 and 20 with respect to the particular indicia on faceplate 14. Returning to FIG. 2, there is further shown the pointer 12 in a position overlying each of the pointers 16, 18 and 20. It should be noted that all three of the pointers 16, 18 and 22 are shown in the same radial position in FIG. 2 for clarification and do not correspond to their respective positions in FIG. 1.

The pointer 12 is attached to the original pointer shaft mechanism within housing 30 by means of a shaft extension 110 which slips functionally over the original pointer shaft and the other end is inserted into a hub on the pointer 12.

On the outside of the pointer 12, that is, the side of the pointer 12 facing away from light detector means 54, 56 and 58, there is provided a lens 112 having a plurality of arc-shaped elongated facets 114, 116 and 118. A light source, generally shown at 120 provides light to be shaped by lens 112 as will be later explained.

Figure 5:
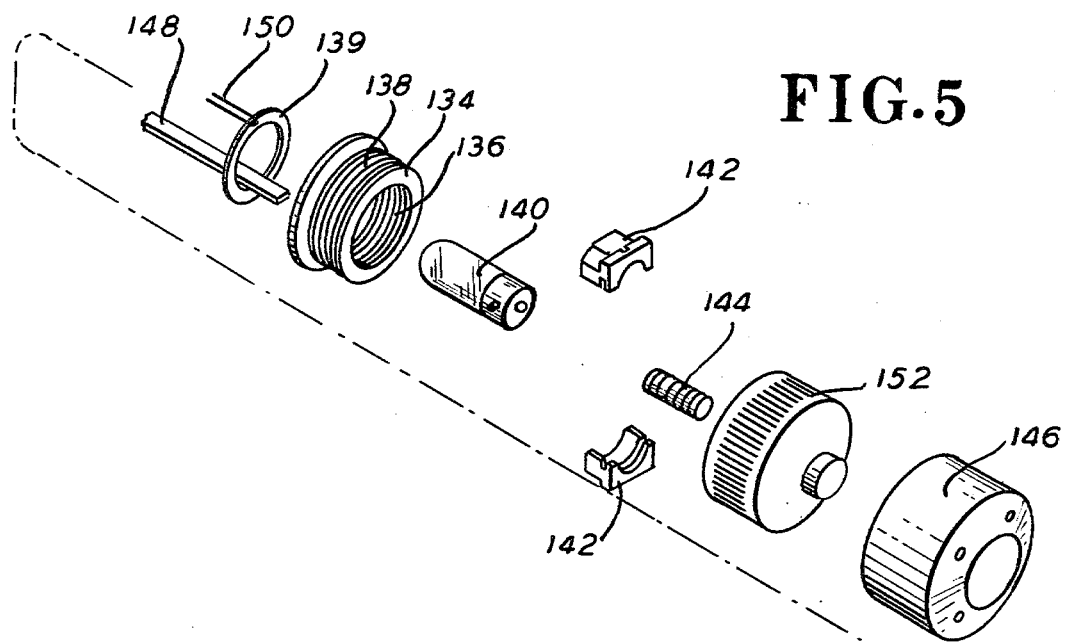
FIG. 5 is an exploded view showing the assembly of the lens and pointer of the present invention.
Figure 5:
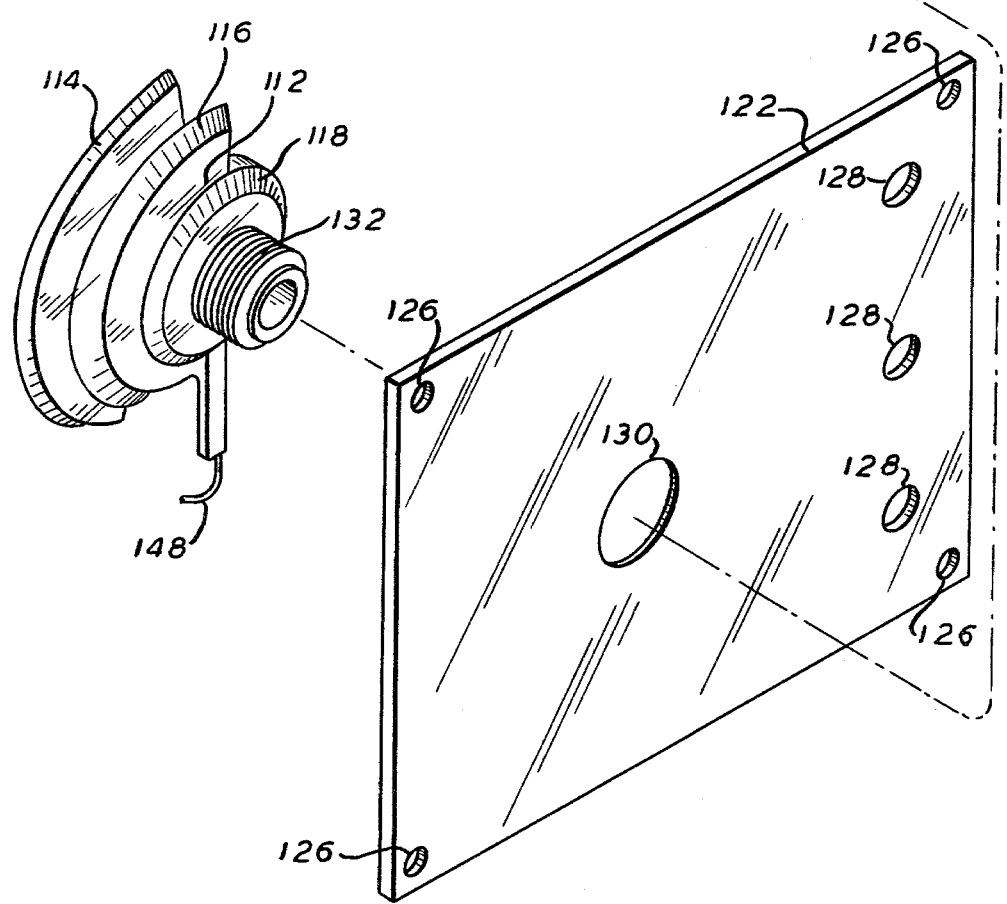

The assembly of the lens 112 and light source 120 can readily be seen by reference to FIG. 5. In FIG. 5 there is shown a transparent cover plate 122 which is adapted to be attached to the housing 46 by means such as screws (shown as 124 in FIG. 1) through holes 126. Other control knob holes 128 are also provided in the cover plate 122 through which the shafts for knobs 22, 24 and 26 protrude when the overall gauge is assembled.

A central opening 130 through cover plate 122 receives a threaded extension 132 of the lens 112. The lens 112 is secured to faceplate 122 by a nut 134 having internal and external threads, respectively, 136 and 138. The internal threads 136 of nut 134 are screwed to the threaded extension 132 of lens 112. A conductor ring 139 contacts nut 134 and is connected to a suitable electrical power source by flex-lead 150.

A conventional light bulb 140 is locked into position inside extension 132 by split locking contacts 142 which retain the contact end of the bulb 140 in a position such that the light portion of bulb 140 containing the filament protrudes within lens 112. The bulb 140 is retained in its position by spring 144 bearing against lamp housing 146. The entire assembly containing bulb 146 is then affixed to the transparent cover plate 122 by cover 146 which is screwed to the outer threads 138 of the nut 134. A second electrical conductor is provided to the bulb 140 by flex conductor 148 which runs through lens 112 to the case of the bulb 140. Flex conductor 150 is soldered to conductor ring 139 which contacts nut 134, housing 152 and spring 144 which contacts back of bulb 140.

Figure 6:
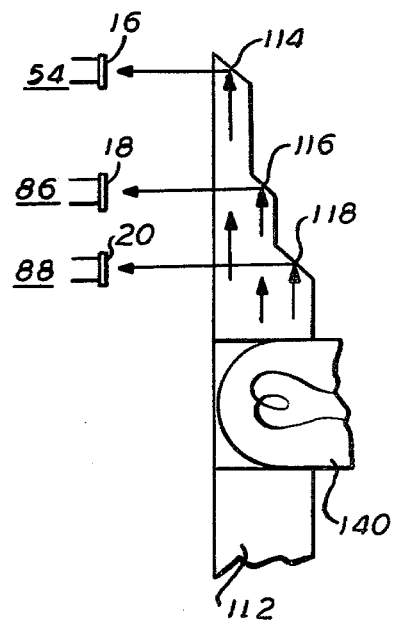
FIG. 6 is an exploded view showing the light source assembly used with the present invention.

The light path of the elongated light beam can be seen in FIG. 6. The centrally located light bulb 140 directs the light within lens 112 toward the plurality of arcuate facets 114, 116 and 118 where the light is reflected at approximately a 90° angle toward the light detectors 54, 86 and 88 which are located immediately behind indicators 16, 18 and 20. In this manner, the light is formed into an elongated beam and the light detectors 54, 86 and 88 are movable generally along the path of that beam.

Inasmuch as the present invention has been particularly adapted and described for use on a medical respirator for which it has distinct advantages, its overall operation will be described with reference to such a respirator.

In such a respirator it is useful to provide a certain simplicity of controls for the operator who has the responsibility of setting certain parameters within which the respirator operates. Basically, the function of a respirator is to breathe the patient, that is, to force air at a predetermined pressure and/or volume into a patient at certain intervals. Such respirators normally include a pressure gauge so that the attending personnel can visually monitor the pressure within the patient circuit, that is, within the tubing that introduces the air into the patient. This monitoring is necessary so that such personnel knows the pressure of air being delivered to the patient and also provides a positive indication that the respirator is operating properly.

The present invention therefore conveniently replaces conventional pressure gauges showing pressure within the patient circuit or, as an alternate, can be retrofilled to such pressure gauges in an existing respirator to thereby include the desirable control feature and ease of setting certain respirator parameters.

Since the human lungs are reasonably compliant, it is necessary with the use of respirators to include some limit on the maximum pressure delivered to the patient's lungs to avoid overinflation and possible damage thereto.

Thus, one of the useful parameters chosen to be incorporated into the gauge 10 of the present invention is a high pressure alarm which sounds an audible alarm when the pressure within the patient circuit exceeds the particular setting and switches the machine out of inspiration so as not to over-pressurize the patient.

As can be seen from FIG. 1, the function of the high pressure alarm is the inside or smallest radius facet 118 of the lens 112. In this instance, the facet 118 extends from approximately 25 $CMH_2O$ to beyond the high figure on the faceplate 14 indicia of 100 $CMH_2O$ and, by adjusting the knob 26, the high pressure indicator 20 can be adjusted to any desired intermediate position within that range. The light source 120 thereby provides light to the lens 112 to reflect the light via facet 118 into an arcuate elongated light beam forming the arc of a circle between the ranges of 25 $CMH_2O$ to 100 $CMH_2O$ on the faceplate 14 of gauge 10. The high pressure indicator 20 moves through corresponding arc as the control knob 26 is turned.

Assuming, therefore, that the attending personnel desires to set the high pressure alarm to sound at 80 $CMH_2O$ by merely turning the control knob 26, he can visually set the indicator 20 at that point in accordance with the indicia on faceplate 14. This positions the corresponding light sensor 88 at that setting and when the pointer 12 passes the sensor 88, it breaks the elongated light beam directed by lens 112 toward sensor 88, thereby causing the sensor 88 to change electrical characteristics. The change in electrical characteristics is detected, amplified and the resulting signal, in accordance with conventional electronic circuitry, actuates the audible high pressure alarm, thereby warning the attending personnel that the pressure in the patient circuit exceeded the desired set limit and switches the machine out of inspiration.

A further useful alarm is shown on the faceplate 14 of the gauge 10 by the legend $\Delta p$. This alarm is also to provide the personnel operating the respirator that there is some malfunction in that the patient is not receiving sufficient "breaths" as desired. The purpose of the $\Delta p$ alarm is to warn the operator that the pressure in the patient circuit is not fluctuating as would be experienced in the normal operation of the respirator. The set point is adjusted in the same manner as explained with respect to the high pressure alarm, however, the $\Delta p$ has its facet 116 in the intermediate pressure ranges, i.e. $-10$ $CMH_2O$ to $+50$ $CMH_2O$ and sounds an audible alarm in case the pointer 12 does not cross the set point every 15 seconds, thereby indicating that a steady pressure, or no pressure, is being maintained within the patient circuit. This alarm can also be set below zero $CMH_2O$ and thus be used during spontaneous ventilation and IMV modes of operation.

Finally, one of the features of some respirators is its ability to respond to the attempt by a patient to breathe, and thus cause the respirator to function to supply the appropriate gas to the patient's lungs. In such feature, the pressure is sensed as it drops as the patient inhales. In the present invention, the patient trigger feature is easily incorporated into gauge 10 by having an indicator 16 and corresponding light detector 54 which can be set, as explained, by the operator turning control knob 22. Thus, pressure, or vacuum, at which the pointer 12 passes the set point of indicator 16 is used to trigger the respirator to inspire the patient, and again, such control is easily set, easily changed and its setting visually perceived by an operator. Sensing the pointer in this manner allows an operator to set the set point at positive pressures when triggering at elevated base lines while using P.E.E.P. (Positive, End, Expiratory Pressures).

Thus, it may be seen that various features, i.e. alarms, patient triggering, can be easily and conveniently set and adjusted by locating the same about the face of the pressure gauge normally found on medical respirators, yet the gauge itself also carries out its normal function of providing a continuous visual monitor of the respirator operation.

While the present invention has been set forth in terms of a specific embodiment, particularly as used on a medical respirator, it will be understood in view of the present disclosure, that while the pointer detecting system is unique to such medical respirator and thus an improvement in that art, that numerous variations of the invention are now enabled to those skilled in the art and such system useable on various other meters, gauges and the like to detect the position of a pointer. Accordingly, the invention is to be broadly construed and limited only by the scope and spirit of the claims appended hereto.

I claim:

1. A meter having a faceplate, said meter further having a pointer movable in a plane generally parallel to the plane of said faceplate, said pointer adapted to move in response to changes in a detected parameter, light means to direct an elongated beam of light generally along the path of movement of said pointer, said elongated beam of light being directed toward one side of said pointer opposite said faceplate, detector means located in said faceplate on the other side of said pointer, said detector means being adjustably positionable along said elongated beam of light, said detector means adapted to sense a diminishment of the intensity of said elongated beam of light when said pointer is positioned substantially directly between said light source means and said detector means.

2. A meter as defined in claim 1 wherein said pointer moves radially about an axis and said light means directs an elongated beam of light in the shape of an arc on a circle, said circle having its center point along said axis of said pointer.

3. A meter as defined in claim 2 wherein said light means directs a plurality of light beams and said detector means is movable along each of said plurality of light beams.

4. A method of detecting the position of a gauge pointer movable in a plane generally parallel to an indicia bearing faceplate, said pointer being movable in response to a change in a detected parameter, said method comprising:
directing an elongated beam of light toward one side of said pointer opposite said faceplate,
locating a detector sensitive to light on the other side of said pointer in said faceplate adjustable along the elongated beam of light,
sensing the diminishment of light intensity to said detector when said pointer interrupts said elongated beam of light to said detector.

5. A system for detecting the position of a pointer moving across a dial having a faceplate in a plane, said system comprising a stationary light source means, lens means adapted to reflect light from said light source means into at least one elongated beam of light directed towards one side of said pointer opposite said faceplate and generally at a right angle to the plane of said faceplate, detector means associated with said faceplate located on the other side of said pointer, said detector means being movable generally along the path of said at least one elongated light beam and positionable at any point therealong, said detector means adapted to sense and transmit a signal in response to a diminishment of light reaching said detector means when said pointer shields said detector means from said at least one elongated beam of light.

6. A system as described in claim 5 wherein said light source means is a point source, and said lens means includes at least one facet for receiving light from said point light source and redirecting said light as an elongated light beam.

7. A system as described in claim 6 wherein said at least one facet is in the shape of a circular arc having the center of its radius at said point light source.

8. A system as described in claim 7 wherein said lens means includes a plurality of facets, each in the shape of a circular arc, and each having its center at said point light source, each of said circular arcs being of different radii, said detector means comprising the same plurality of light detectors being generally movable along one of said plurality of circular arcs.

* * * * *